(12) United States Patent
Haarala et al.

(10) Patent No.: US 7,824,365 B2
(45) Date of Patent: *Nov. 2, 2010

(54) PERCUTANEOUS ACCESS

(75) Inventors: Brett T. Haarala, Framingham, MA (US); Brian Bergeron, Worcester, MA (US); Paul DiCarlo, Middleboro, MA (US)

(73) Assignee: Navilyst Medical, Inc., Marlborough, MA (US)

( * ) Notice: Subject to any disclaimer, the term of this patent is extended or adjusted under 35 U.S.C. 154(b) by 1524 days.

This patent is subject to a terminal disclaimer.

(21) Appl. No.: 10/852,247

(22) Filed: May 24, 2004

(65) Prior Publication Data

US 2004/0267238 A1    Dec. 30, 2004

Related U.S. Application Data

(60) Continuation of application No. 10/462,464, filed on Jun. 16, 2003, now Pat. No. 6,758,841, which is a division of application No. 09/896,822, filed on Jun. 29, 2001, now Pat. No. 6,607,504.

(51) Int. Cl.
  *A61M 31/00* (2006.01)

(52) U.S. Cl. .................................................. 604/93.01

(58) Field of Classification Search .............. 604/93.01, 604/82–86, 241, 174, 242, 243, 167.01, 167.02–167.06, 604/168.01, 905
See application file for complete search history.

(56) References Cited

U.S. PATENT DOCUMENTS

| 4,416,657 | A | * | 11/1983 | Berglund | 604/9 |
| 5,180,365 | A | * | 1/1993 | Ensminger et al. | 604/288.03 |
| 5,251,873 | A | * | 10/1993 | Atkinson et al. | 251/149.1 |
| 6,004,301 | A | * | 12/1999 | Carter | 604/256 |
| 6,607,504 | B2 | * | 8/2003 | Haarala et al. | 604/93.01 |
| 7,387,624 | B2 | * | 6/2008 | Nelson | 604/536 |

* cited by examiner

*Primary Examiner*—Manuel A Mendez
(74) *Attorney, Agent, or Firm*—Bingham McCutchen LLP

(57) ABSTRACT

Medical devices and related methods enable physicians and/or other medical personnel to access percutaneously the interior of a patient. One particular device includes a housing which defines a cavity, a first opening into the cavity, and a second opening into the cavity. The housing is implantable in a patient. The cavity is placed subcutaneously within the patient. The first opening is substantially flush with the surface of the skin of the patient and creates a percutaneous passageway from the exterior of the skin of the patient into the cavity, and the second opening creates a passageway from the cavity into the interior of the patient. A connector is coupled to the second opening and disposed substantially within the cavity to enable a connection between a first device and a second device disposed within the interior of the patient.

15 Claims, 14 Drawing Sheets

PERCUTANEOUS ACCESS

The present application is a continuation of application Ser. No. 10/462,464, filed Jun. 16, 2003 now U.S. Pat. No. 6,758,841 which is a divisional of application Ser. No. 09/896,822, filed Jun. 29, 2001 now U.S. Pat. No. 6,607,504, both of which are entitled "Percutaneous Access".

TECHNICAL FIELD

The invention relates generally to percutaneous access, and more specifically to methods and devices associated with percutaneous access.

BACKGROUND INFORMATION

Long term access to a patient's bloodstream (longer than one month, for example) is required for many medical treatments including antibiotic therapy, hemodialysis access, chemotherapy regimens, and other treatments that require repeated infusion or blood processing. In some cases, internal access to the patient is required for years. Current devices and methods generally negatively impact the quality of the patient's life, and the patient sometimes develops complications as a result of the long term access. Vascular access devices used for longer term treatments include tunneled central catheters (including dialysis catheters), implanted infusion ports (including dialysis ports), dialysis grafts, and fistulas. A cuffed catheter can be used for non-vascular access, such as to the abdominal cavity for peritoneal dialysis to prevent infection.

Tunneled catheters can cause infection of the bloodstream or peritoneum and the skin entry site. The external portion of the catheter can fracture or otherwise fail due to its movement after placement. Also, the placed catheter can be accidentally or intentionally removed from the body, causing the patient pain and other complications. There is also the possibility of increased wear, damage, or disassembly caused by the patient "playing with" the placed device. The skin entry site requires constant maintenance and clamps are required to prevent bleeding through the catheter and to prevent air embolus. The portion of the catheter external to the patient's body frequently is uncomfortable for the patient. The external catheter and the skin entry site can prevent the patient from bathing normally or engaging in normal physical activities.

Subcutaneously implanted access ports require the use of needles to access the port through the patient's skin. Using needles, such as the large needles used for dialysis ports, creates the potential for infection and causes the patient pain. The access port reservoir has the potential of accumulating debris and harboring infection. In the event an internally-connected catheter connecting to this type of port needs to be replaced, a surgical procedure is required.

Grafts and fistulas on the patient's arm are disfiguring, and they require frequent access with large bore needles which causes pain and eventually destroys the access route. Grafts and fistulas also require invasive vascular surgery to be created and revised. Additionally, interluminal declotting is often necessary.

With respect to medical devices that are permanently implanted into a patient, such as a pacemaker for example, access is limited to surgical means in order to reach the device to replace batteries or repair components. Electrical leads that pass through the skin to supply power and control for the internally-implanted device can cause infection.

SUMMARY OF THE INVENTION

The invention relates generally to percutaneous access, and more specifically to methods and devices associated with percutaneous access. In one embodiment, an access device allows physicians and other medical personnel to obtain long term percutaneous access to a patient's body. The access device reduces the opportunity for infection by completely shielding fluid connections (that extend into the interior of the patient's body) from the patient's skin and from the external environment. The access device has no protruding external elements, and can be protected by a low-profile cover that is substantially flush with the patient's skin. The access device thus is cosmetically appealing and allows substantially normal physical activity. The cover is difficult to remove accidentally or intentional from the access device. The access device allows access to the interior of the patient without requiring a needle to pierce the skin. Further, internal components, such as a catheter or a valve, can be replaced without a surgical procedure.

In one aspect, the invention involves a medical device. The medical device includes a housing defining a cavity, a first opening into the cavity, and a second opening into the cavity. The housing is implantable in a patient to dispose the cavity subcutaneously within the patient. The first opening is substantially flush with the surface of the skin of the patient and creates a percutaneous passageway from the exterior of the skin of the patient into the cavity. The second opening creates a passageway from the cavity into the interior of the patient. The medical device further includes a connector coupled to the second opening and disposed substantially within the cavity and allows for a connection between a first device and a second device disposed within the interior of the patient. In one embodiment, the housing defines a flange for extending subcutaneously into the patient to anchor the housing in the patient.

In another embodiment, the medical device further includes a cover that is removably couplable to the housing. The cover selectively seals and exposes the first opening and is cover substantially coplanar with the surface of the skin of the patient when sealing the first opening. The cover is removable to allow the first and second devices to be connected via the connector. The cover includes a locking mechanism to prevent the cover from being inadvertently removed. In other embodiments the cover is canoe or elliptically shaped. In one embodiment, the cover further includes an electrical connector. In another embodiment, the cover further includes a display.

In yet another embodiment, the connector includes a luer connector. In other embodiments, the medical device further includes a valve. In still other embodiments, the medical device further includes a cap removably coupled to the luer connector to selectively seal and expose the luer connector. The cap removably couples to the luer connector with a threaded connection. In some embodiments, the luer connector is telescopic and capable of being extended out of the cavity when the cover is removed from the first opening. In other embodiments, the luer connector includes a pivoting luer connector which opens a fluid path through the second opening when pivoted to a first position and seals the fluid path through the second opening when pivoted to a second position. In yet another embodiment, the connector includes an electrical connector. In another embodiment, the connector is releasably couplable to the second opening.

In still another embodiment, the first device includes a connection tube and the second device includes a catheter. The catheter includes a single lumen catheter a multilumen catheter.

In one embodiment, the first device includes an infusion device for infusing medication into the patient. In another embodiment, the first device includes a device for removing bodily fluids of the patient. In still another embodiment, the first device includes a device for removing, purifying, and reintroducing blood into the patient.

In another embodiment, the connector includes an electrical-connector. In one embodiment, the electrical connector is releasably couplable to a battery disposable entirely within the cavity for supplying power to the second device. In another embodiment, the electrical connector is releasably couplable to a control device disposable entirely within the cavity for supplying control signals to the second device.

In another aspect, the invention relates to a method of obtaining percutaneous access to the interior of a patient. The method includes making a straight incision in the patient and implanting in the patient through the straight incision a medical device. The medical device includes a housing defining a cavity, a first opening into the cavity, and a second opening into the cavity. The housing is implantable in a patient to dispose the cavity subcutaneously within the patient. The first opening is substantially flush with the surface of the skin of the patient and creates a percutaneous passageway from the exterior of the skin of the patient into the cavity. The second opening creates a passageway from the cavity into the interior of the patient. The method further includes mating a connector to a proximal end of a catheter and inserting a distal end of the catheter through the second opening. The method further includes sliding the catheter through the second opening into the interior of the patient and coupling the proximal end of the catheter and the connector to the second opening thereby disposing the connector substantially within the cavity and sealing the second opening and creating a fluid path from the interior of the patient to the connector. The method further includes connecting a first device external to the patient to the connector through the first opening.

In one embodiment, the method further includes anchoring the housing within the patient with sutures. The sutures include subcutaneous sutures In another embodiment, the method further includes anchoring the housing within the patient with subcutaneous hooks.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1:
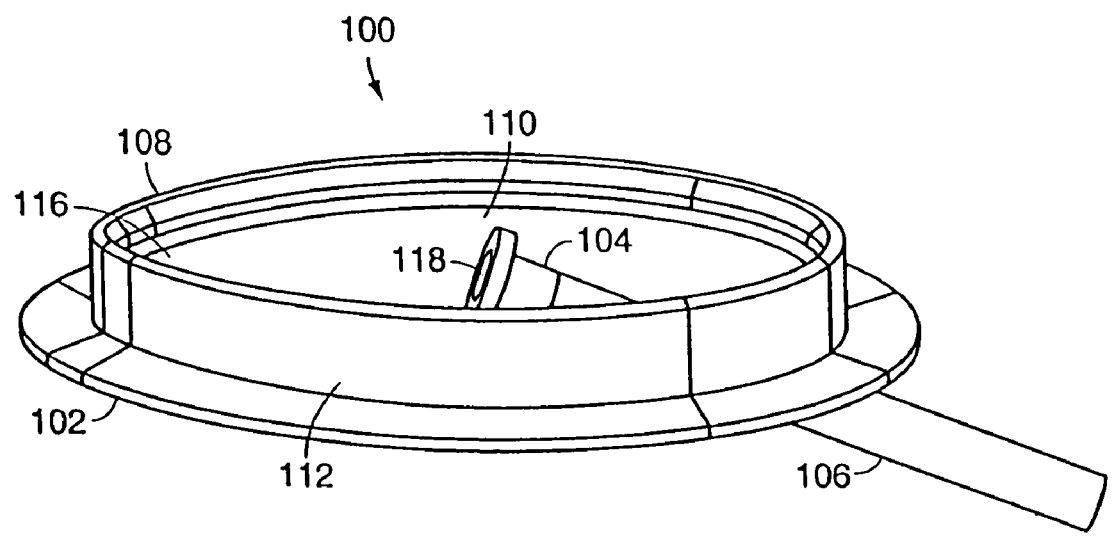
FIG. 1 is an illustrative perspective side view of a percutaneous access device according to one embodiment of the invention.
Figure 2:
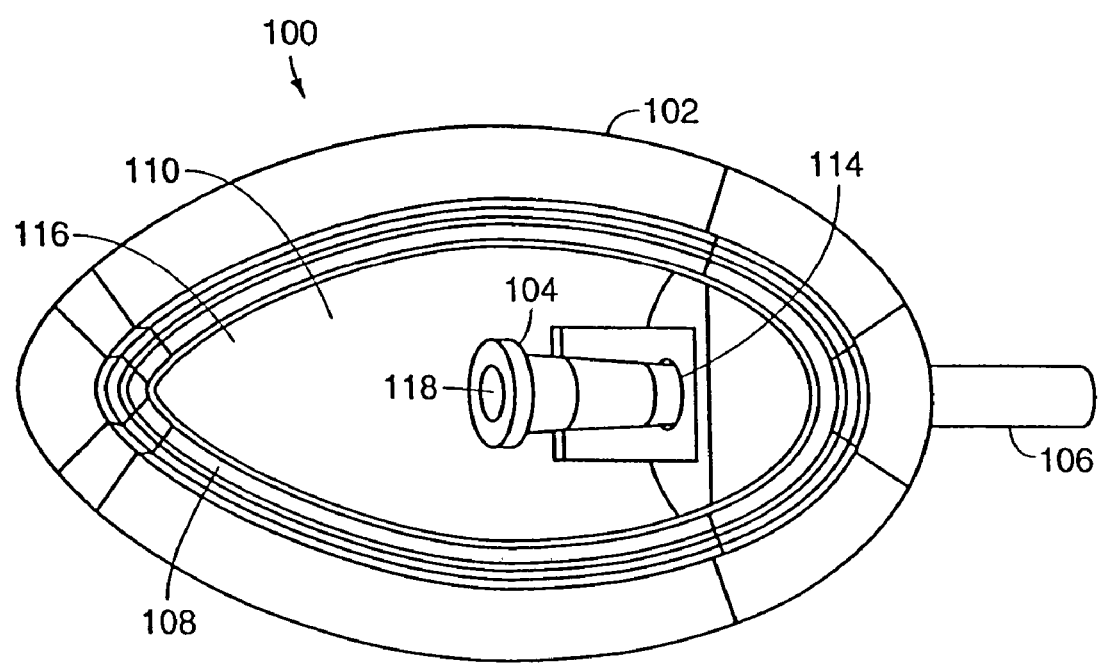
FIG. 2 is an illustrative top view of the percutaneous access device shown in FIG. 1.
Figure 3:
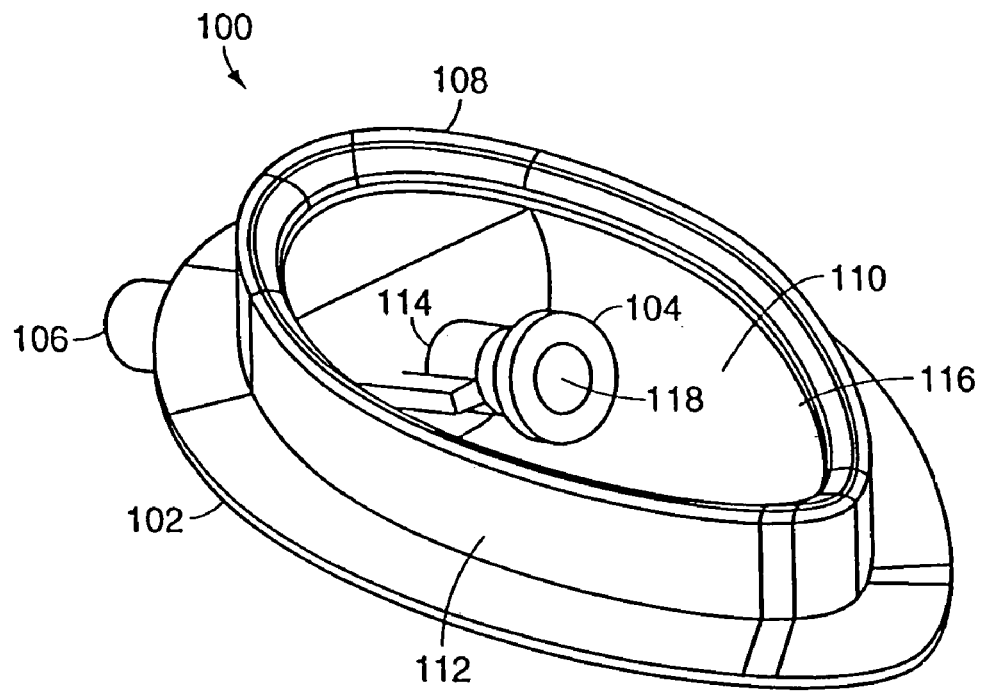
FIG. 3 is an illustrative perspective view of the percutaneous access device shown in FIG. 1.
Figure 4:
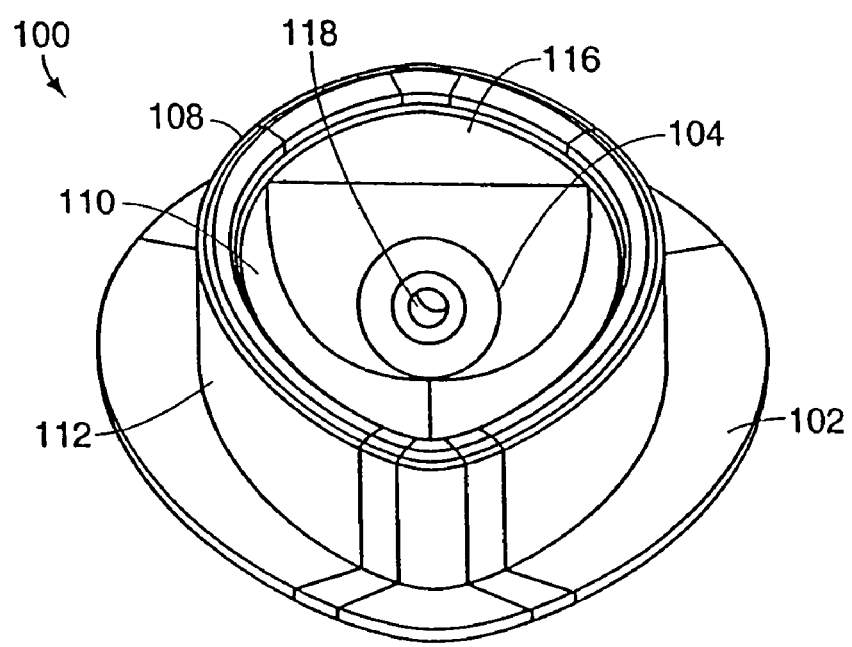
FIG. 4 is an illustrative perspective front view of the percutaneous access device shown in FIG. 1.

The invention relates generally to percutaneous access, and more specifically to methods and devices associated with percutaneous access. In one embodiment, an access device allows physicians and/or other medical personnel to obtain long term percutaneous access to the interior of a patient's body. The access device reduces the opportunity for infection by completely shielding fluid connections (that extend into the interior of the patient's body) from the patient's skin and from the external environment. The access device has no protruding external elements, and can be protected by a low-profile cover that is substantially flush with the patient's skin. The access device thus is cosmetically appealing and allows substantially normal physical activity. The cover is difficult to remove accidentally or intentionally from the access device. The access device allows access to the interior of the patient without requiring a needle to pierce the skin. Further, internal components, such as a catheter or a valve, can be replaced without a surgical procedure.

Referring to FIGS. 1-4, in one embodiment, a medical device for allowing percutaneous access to a patient's body is an access device 100 which includes a housing 112, a cavity 110, a first opening 116, a flange 102, a second opening 114, and a connector 104. The housing 112 defines the cavity 110, the first opening 116 (which leads into the cavity 110), and the second opening 114 (which also leads into the cavity 110).

Figure 17C:
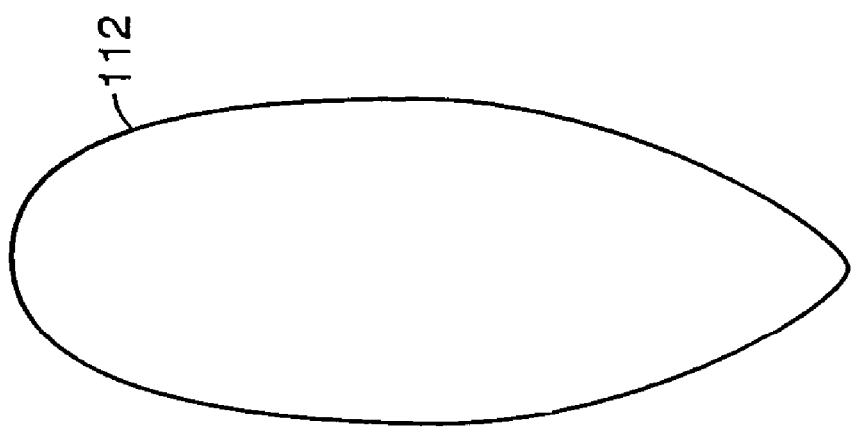
FIG. 17C is an illustrative top view of a housing cover with an almond shape, according to yet another embodiment of the invention.
Figure 17B:
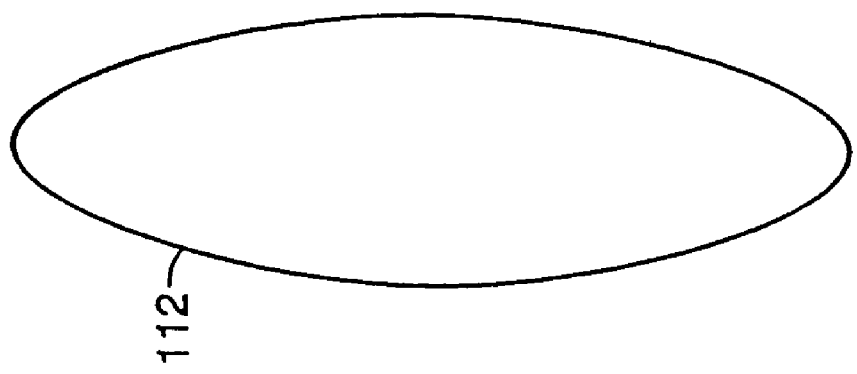
FIG. 17B is an illustrative top view of a housing cover with an canoe shape, according to another embodiment of the invention.
Figure 17A:
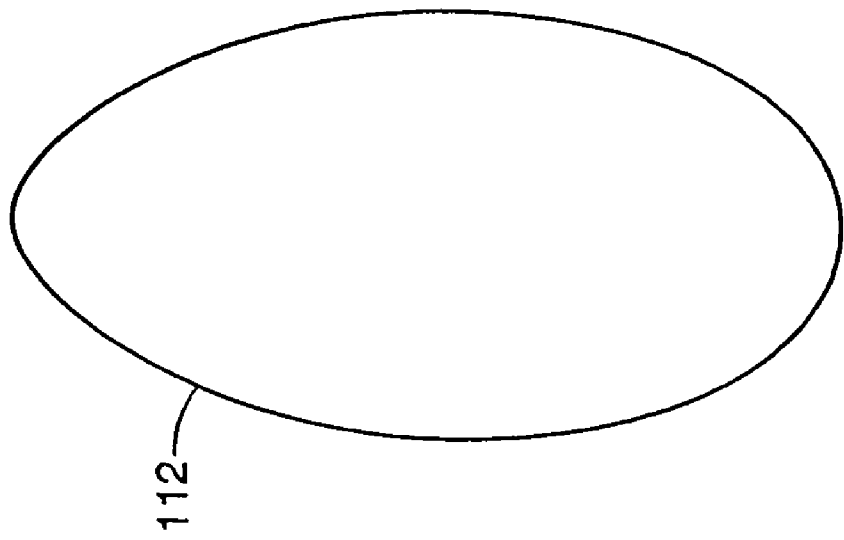
FIG. 17A is an illustrative top view of a housing cover with an elliptical shape, according to one embodiment of the invention.

The housing 112 is implanted in a patient to dispose the cavity 110 subcutaneously within the patient. After the housing 112 is implanted in the patient, the first opening 116 is substantially flush with the surface of the skin of the patient and creates a percutaneous passageway from the exterior of the skin of the patient into the cavity 110. The second opening 114 creates a passageway from the cavity 110 into the interior of the patient. The connector 104 is coupled to the second opening 114 and is disposed substantially within the cavity 110. The connector 104 allows a first device which is external to the patient, such as an infusion pump for example, to be connected to a second device disposed within the interior of the patient, such as a catheter 106 for example. The flange 102, which is coupled to the housing 112, holds the housing 112 in place once the housing 112 is implanted in a patient. In one embodiment, the housing 112 is made of a bio-compatible material such as Polysulfone or Titanium. The housing 112 can also be made of a molded bio-compatible plastic material. In another embodiment, the housing 112 can made of a soft material that can be penetrated by sutures or needles. In some embodiments, the housing 112 is canoe shaped, elliptically shaped, or almond shaped, as indicated in FIGS. 17A, 17B, and 17C. In other embodiment, the housing 112 includes a concave bottom, as indicated in FIG. 5 and in still other embodiments the housing 112 include a flat bottom, as indicated in FIG. 1.

Figure 5:
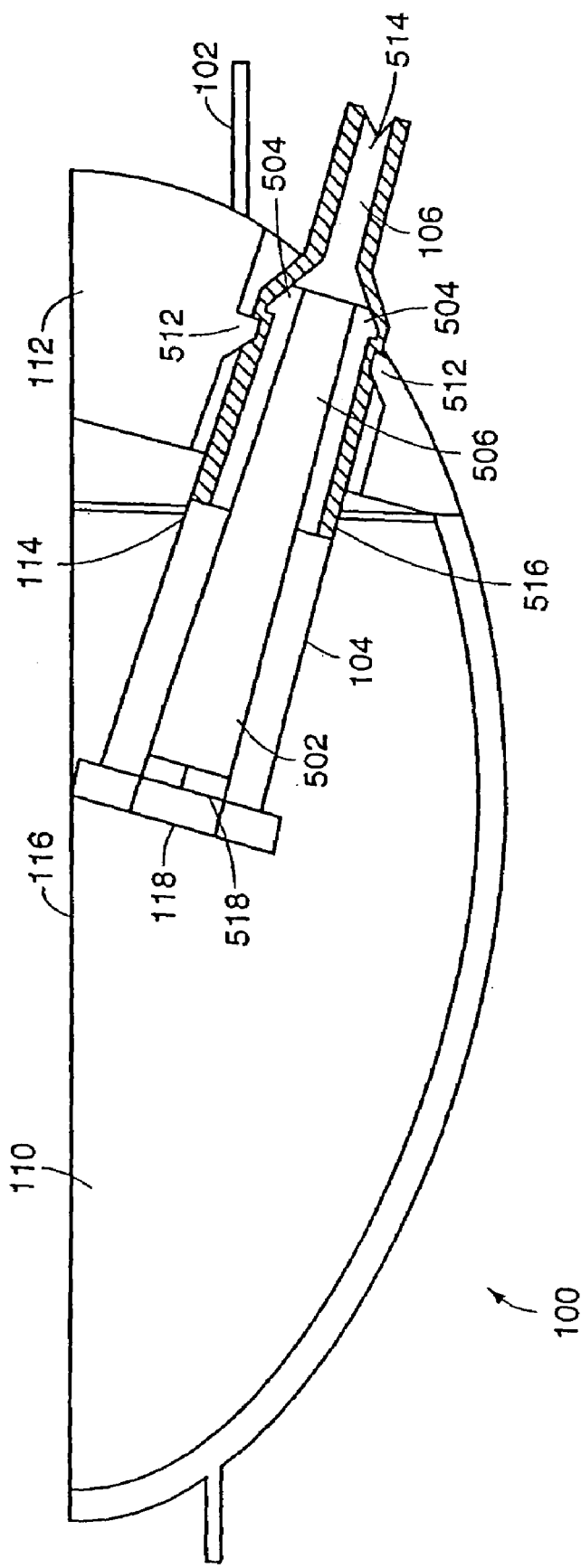
FIG. 5 is an illustrative cross-sectional side view of a percutaneous access device according to another embodiment of the invention.

Referring to FIG. 5, in one embodiment, the connector 104 is a luer connector and is coupled to the second opening 114 and the catheter 106. A proximal end 516 of the catheter 106 is first positioned over a distal end 506 of the connector 104. The catheter is held in place over the connector 104 by a plurality of barbs 504 (or a raised ring) on the distal end 506 of the connector 104. The distal end 506 of the catheter 106 is fed through the opening 114 until the plurality of barbs 504 on the distal end 506 of the connector 104 engage a plurality of barbs 512 within the second opening 114. The connector 104 is secured in place by engaging the plurality of barbs 504 with the plurality of barbs 512. After the connector 104 is secured in place, the connector 104 is positioned such that the connector 104 is disposed substantially within the cavity 110. Specifically, in some embodiments, a small portion of the connector 104 can extend out of the first opening 116. However, in other embodiments, no portion of the connector 104 extends out of the first opening 116 and is disposed entirely within the cavity 110. In some embodiments, the connector 106 is sealable when not in use. For example, the connector 106 can have a threaded or friction fit sealing cap that is removed during use and replaced when not in use. The cap can also include a penetrable surface, such as rubber or silicone for example, which can be penetrated by a needle. Further, the connector 106 can include a valve 518 which opens when the connector 106 is connected to an external device and closes when the connector 106 is disconnected from the external device. In some embodiments, the value 518 can be a slit valve made of foam or rubber. The connector 106 is also compatible with typical medical luer attachments. In other embodiments, the connector 104 and the catheter 106 can include a single lumen or multiple lumens.

Figure 6:
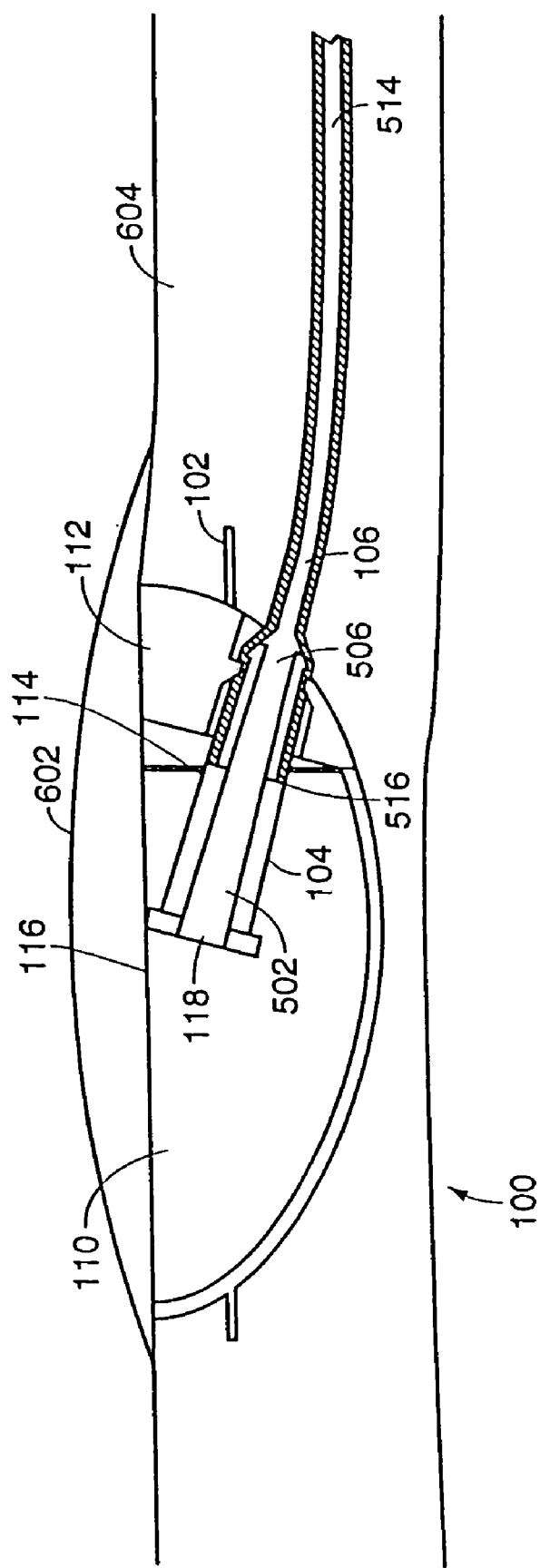
FIG. 6 is an illustrative cross-sectional side view of the percutaneous access device of FIG. 5, implanted in a patient.

Referring to FIGS. 1 and 6, in one embodiment, the percutaneous access device 100 is implanted into a patient 604 as follows. First, a linear incision is made in the patient. Such an incision is less traumatic to the patient (as opposed to coring). A distal end of a guidewire is inserted through the incision, into the patient 604, and into an area in which the catheter 106 is to be placed, such as vein for example. If necessary, a dilator may be placed over the guidewire to dilate the area where the catheter 106 is to be inserted. A proximal end of the guidewire is inserted through the second opening 114 and the housing 112 is then inserted into the patient 604 through the incision. The housing 112 is positioned so that the second opening 114 is axially aligned with the guidewire, the flange 102 is subcutaneous, and the first opening 116 is substantially flush with the surface of the patient's skin 604. The flange 102 promotes stability of the housing 112 and adhesion of the skin and subdermal layers immediately adjacent to the incision site. In some embodiments, subcutaneous sutures sewn through holes in the flange 102 can be used to anchor the subdermal layers to the flange 102. In other embodiments subcutaneous hooks may be used to anchor the subdermal layers to the flange 102. In still other embodiments, the flange 102 can be coated with materials that promote tissue growth to provide better sealing of the incision, such as collagen or other tissue growth catalysts, for example. Materials that promote ingrowth of cells, such as a permeable fabric, a textured polymer, or a steel mesh can also be bonded to or embedded in the flange 102. The added ingrowth materials cause the skin surrounding the flange 102 to bond securely with the flange 102. The surface of the patient's skin 604 may also be secured to the housing 112 by using glue, such as Dermabond (a trademark of and a product commercially available from Closure Medical Corporation of Raleigh, N.C.) or medical tape around the incision site.

After the housing 112 is anchored in place, the distal end 514 of the catheter 106 is inserted through the second opening 114 over the guidewire and fed into the patient. Next, the guidewire is removed and the proximal end 516 of the catheter 106 is coupled to the distal end 506 of the connector 104 and the distal end 506 of the connector 104 is fed through the opening 114 and secured in place (as previously described) thereby sealing the opening 114 and creating a fluid path 502 from the interior of the patient to the connector 104.

The implanted access device 100 can then be covered with a temporary dressing or Tegaderm (a trademark of and a product commercially available from 3M Health Care Ltd. of Loughborough, UK) which is a skin-like bandage. The cavity 110 can also be filed with gauze and/or antimicrobial agents. In another embodiment, the housing 112 can be covered with a low-profile, housing cover 602, which can be shaped to conform to the contour of the patient's skin. The housing cover 602 couples to an edge 108 of the housing 112 and creates a watertight seal and protects the connector 106 and the cavity 110 from debris and damage from the environment. In some embodiments, the housing cover 602 includes a locking mechanism which prevents the housing cover 602 from being accidentally or intentionally removed by the patient. For example, the housing cover 602 can be secured to the housing 112 by using a friction fit or a thread fit. The housing cover 602 can also be secured to the housing 112 using clamps that clamp onto the edge 108. The clamps can be configured to selectively engage and disengage the edge 108 when a key is inserted into the housing cover and turned. In other embodiments, the housing cover 602 can be coupled to the housing 112 with a wire or a hinge, for example. Additionally, gauze can be placed around the first opening 116 between the patient's skin and the housing cover 602.

In another embodiment, after the linear incision is made, the guidewire is inserted into the vein (or other organ) and then the distal end 514 of the catheter 106 is inserted into the vein over the guidewire. Next, the proximal end 516 of the catheter is inserted into the second opening 114 and fed into the housing 112. The guidewire is removed and the distal end 506 of the connector 104 is then coupled to the proximal end 516 of the catheter and then fed through the opening 114 and secured. The housing 112 is then implanted into the patient using the procedure previously described.

Figure 7:
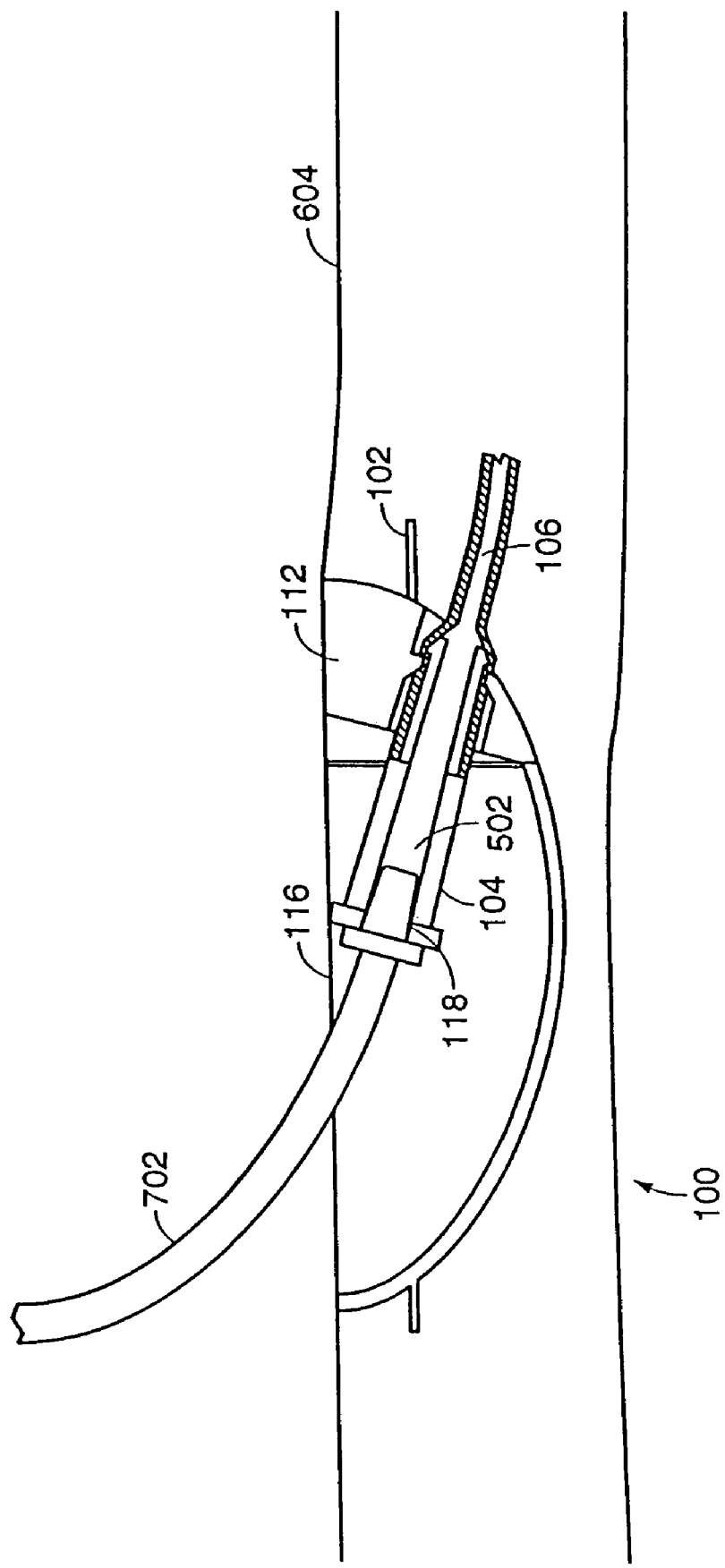
FIG. 7 is an illustrative cross-sectional side view of the percutaneous access device shown in FIG. 5, implanted in a patient and connected to an external medical device.

Referring to FIGS. 6 and 7, the connector 104 is accessed by first removing the housing cover 602. Next, an external medical device, such as a connection tube 702 to an infusion pump, is connected to the connector 104 creating a fluid connection 502 through opening 118. After the procedure utilizing the infusion pump has been completed, the connection tube 702 is disconnected from the connector 104 and the housing cover 602 is placed back on the housing 112 to seal the cavity 110 and protect the connector 104. The access device 100 can be used with a variety of other medical devices, such as body fluid removal devices and blood purification devices, for example.

The access device 100, after initial surgical implantation, enables physicians and/or other medical personnel to repeatedly (and without further surgery) access various internal regions of the patient, such as veins, arteries, and various organs for example. The connector 104 and fluid connection that extends into the patient's body is shielded from the patient's skin and from the external environment, and thereby reduces opportunity for infection. The access device 100 has no protruding external elements, and can be protected by the low-profile housing cover 602 which is substantially flush with the patient's skin and thereby allows the patient to engage in substantially normal physical activity.

Referring again to FIGS. 5 and 6, if the access device 100 remains implanted for an extended period of time, the connector 104 and/or the catheter 106 may need to be replaced. Replacement of these components can be achieved without surgery. First, the housing cover 602 is removed from the housing 112. Next, the connector 104 is removed from the second opening 114 and the connector 104 is decoupled from the catheter 106. A guidewire is fed through the catheter into the patient. The catheter 106 is then removed from the patient. A new catheter 106 is inserted into the patient over the guidewire through the second opening 114 and the guidewire is then removed. A new connector 104 is coupled to the catheter 106 and secured in the second opening 114 as previously described. A benefit of this feature is that the connector 104 and/or the catheter 106 can be replaced without surgery, resulting in less trauma to the patient and reduced chance of infection.

Figure 8A:
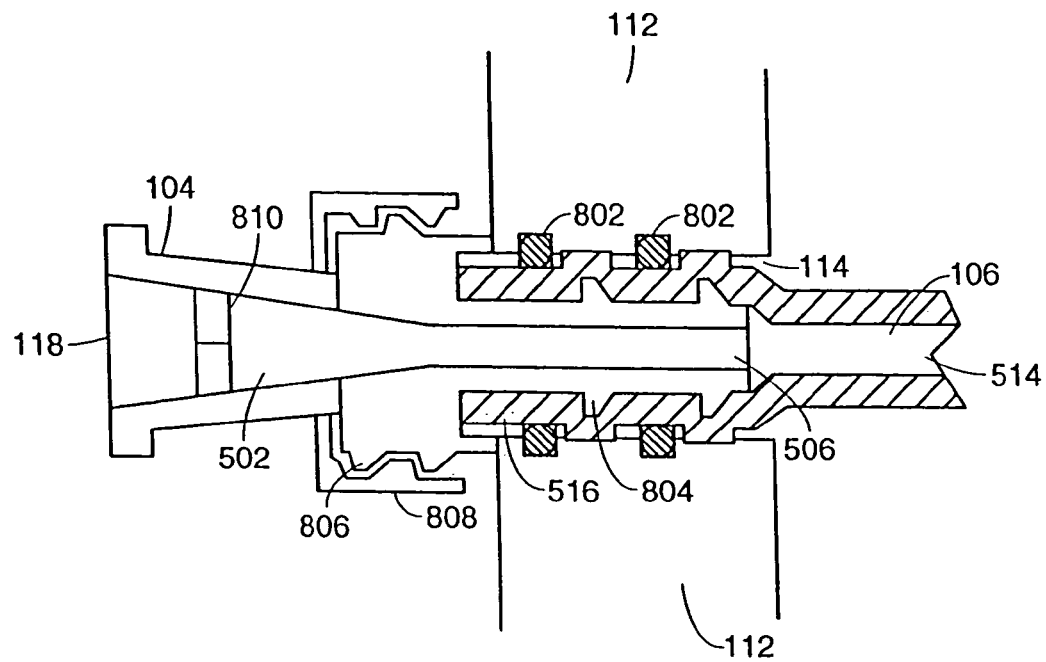
FIG. 8A is an illustrative cross-sectional view of a connector-catheter connection including a valve in a closed position according to one embodiment of the invention.
Figure 8B:
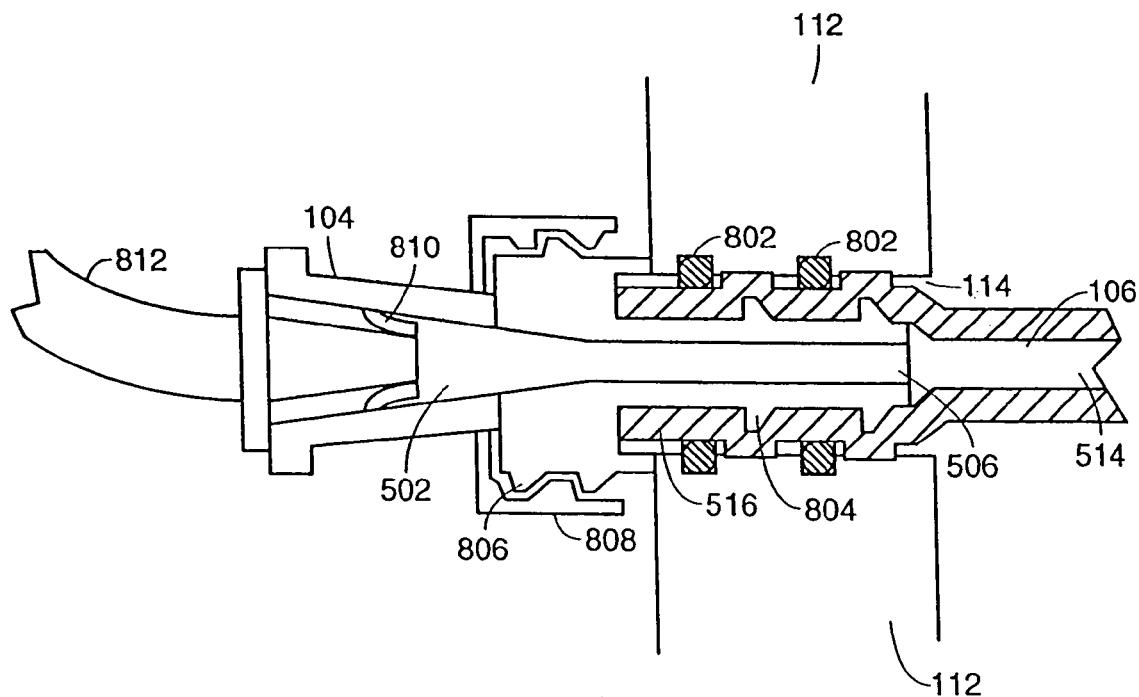
FIG. 8B is an illustrative cross-sectional view of the connector-catheter connection shown in FIG. 8A, including the valve in an open position.

Referring to FIGS. 8A and 8B, in another embodiment, the connector 104 is a luer connector and is coupled to the second opening 114 and the catheter 106. A proximal end 516 of the catheter 106 is first positioned over a distal end 506 of the connector 104. The catheter 106 is held in place over the connector 104 by a plurality of barbs 804 (or a rings) on the distal end 506 of the connector 104. The distal end of the catheter 106 is fed through the opening 114 until the plurality of barbs 504 on the distal end 506 of the connector 104 meet a plurality of O-rings 802. The connector 104 is secured in place by engaging the plurality of barbs 504 with the plurality of O-ring 802. After the connector 104 is secured in place, the connector 104 is positioned such that the entire connector 104 is disposed entirely within the cavity 110. The connector 104 also includes a threaded locking cap 808 which engages threads 806. The locking cap 808 is used to secure a connection between the connector 104 and an external medical device. The connector 104 can also include a valve 810 which remains sealed when no external medical device is connected to the connector 104 and opens when the connector 104 is connected to an external medical device, such as a connection tube 812 to an infusion pump.

Figure 9A:
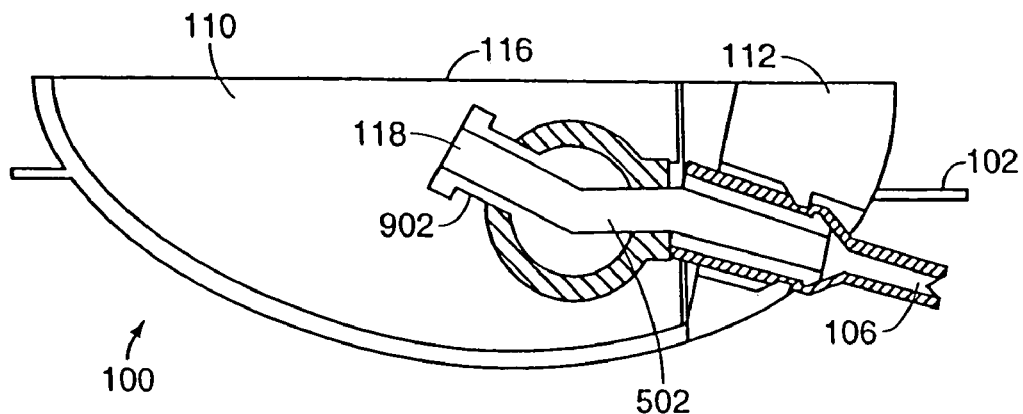
FIG. 9A is an illustrative cross-sectional view of a percutaneous access device including a pivoting luer connector in an open position, according to one embodiment of the invention.
Figure 9B:
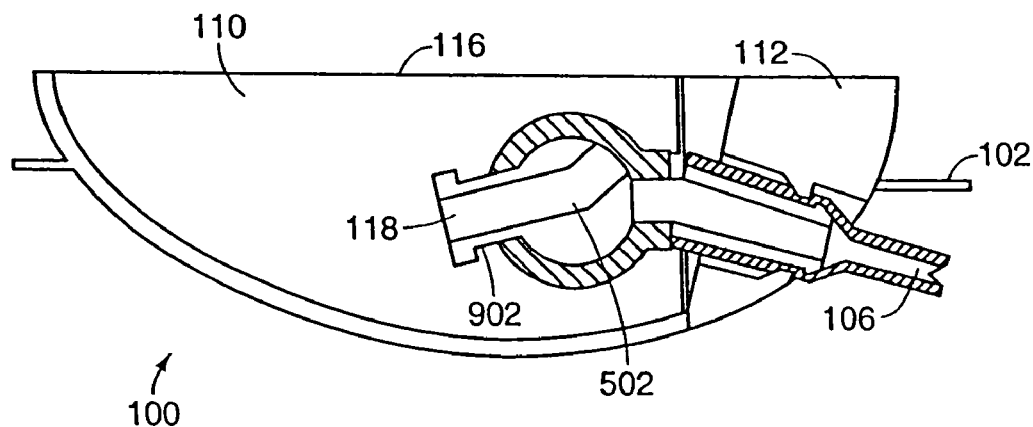
FIG. 9B is an illustrative cross-sectional view of the percutaneous access device shown in FIG. 9A, with the pivoting luer connector in a closed position.

Referring to FIGS. 9A and 9B, in another embodiment, the access device 100 includes a pivoting luer connector 902. The pivoting luer connector 902, when pivoted to a first position, opens the fluid path 502 through the second opening 114 and, when pivoted to a second position, closes the fluid path 502 through the second opening 114. In operation, when the pivoting luer connector 902 is not in use, the pivoting luer connector 902 is pivoted to the second position thereby keeping the fluid path 502 closed. The pivoting luer connector 902 is only pivoted to the first position after an external medical device has been connected to the pivoting connector 902.

Figure 10A:
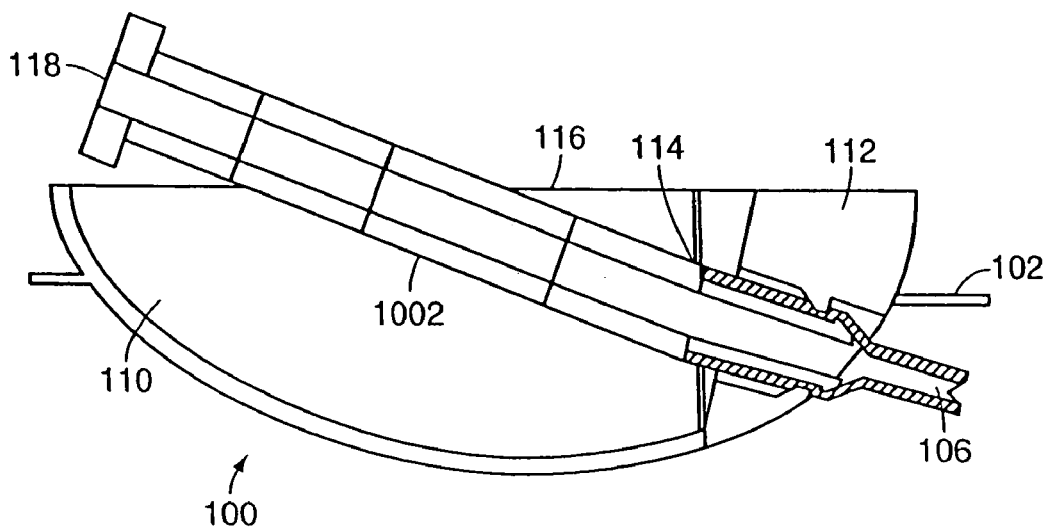
FIG. 10A is an illustrative cross-section view of a percutaneous access device including a telescopic luer connector in an extended position, according to one embodiment of the invention.
Figure 10B:
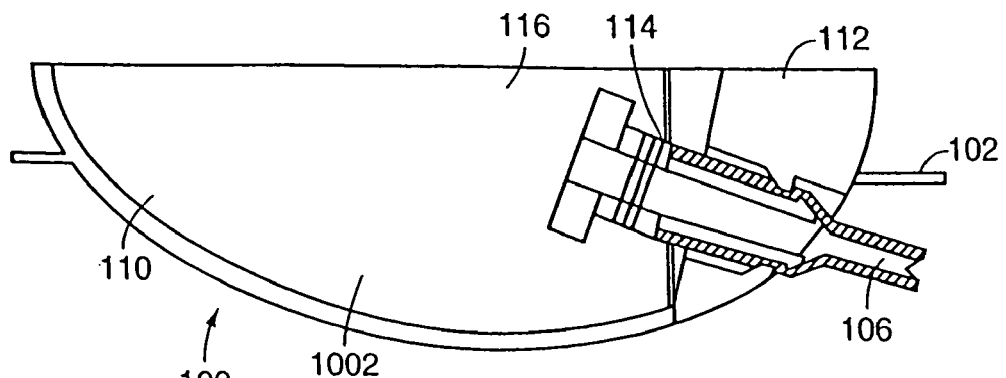
FIG. 10B is an illustrative cross-section view of a percutaneous access device including a telescopic luer connector in a retracted position, according to one embodiment of the invention.

Referring to FIGS. 10A and 10B, in still another embodiment, the access device 100 includes a telescopic luer connector 1002. The telescopic connector 1002, when not in use, is disposed entirely within the cavity 110. However, when the telescopic connector 1002 is in use, the telescopic connector 1002 can be extended out of the cavity 110 to allow a physician or other medical personnel to connect an external medical device more easily. In another embodiment, the telescopic connector 1002 includes a stop or plug disposed inside the connector 1002. The stop is coaxial with the opening 118 and acts as a valve which seals the opening 118 when the telescopic connector is 1002 is retracted. When the telescopic connector 1002 is extended, the seal between the opening 118 and the stop is broken thereby allowing fluid to flow past the stop and through the opening 118.

Figure 13:
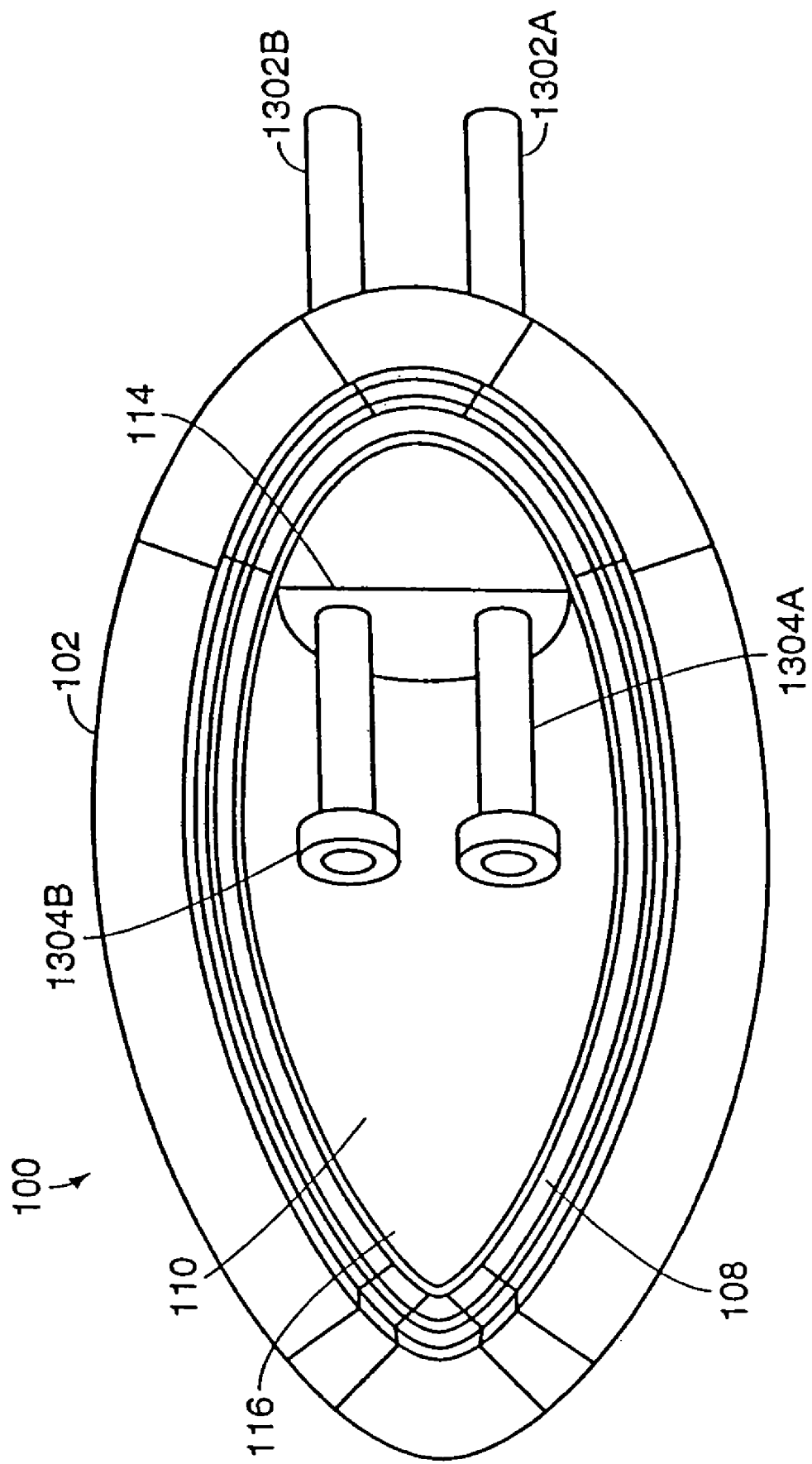
FIG. 13 is an illustrative top view of the percutaneous access device including two connectors, according to another embodiment of the invention.

Referring to FIG. 13, in other embodiments, the access device 100 includes two luer connectors 1304a and 1304b and two corresponding catheters 1302a and 1302b. In this configuration, blood, for example, can be easily drawn out of a patient, purified, and put back into the patient. In another embodiment, the access device 100 includes two luer connections that both connect to a single catheter. The single catheter a single lumen catheter or multilumen catheter.

In other embodiment, the access device 100 includes a luer connector with a pressure-responsive slit valve. The valve includes a diaphragm including a slit which is flexed in one direction by hydrostatic pressure and flexed in an opposite direction by negative pressure to selectively open the slit. Examples of such a pressure-responsive slit valves are shown in U.S. Pat. No. 5,205,834, U.S. Pat. No. 5,201,722, and U.S. Pat. No. 5,169,393 which are herein incorporated by reference.

Figure 11:
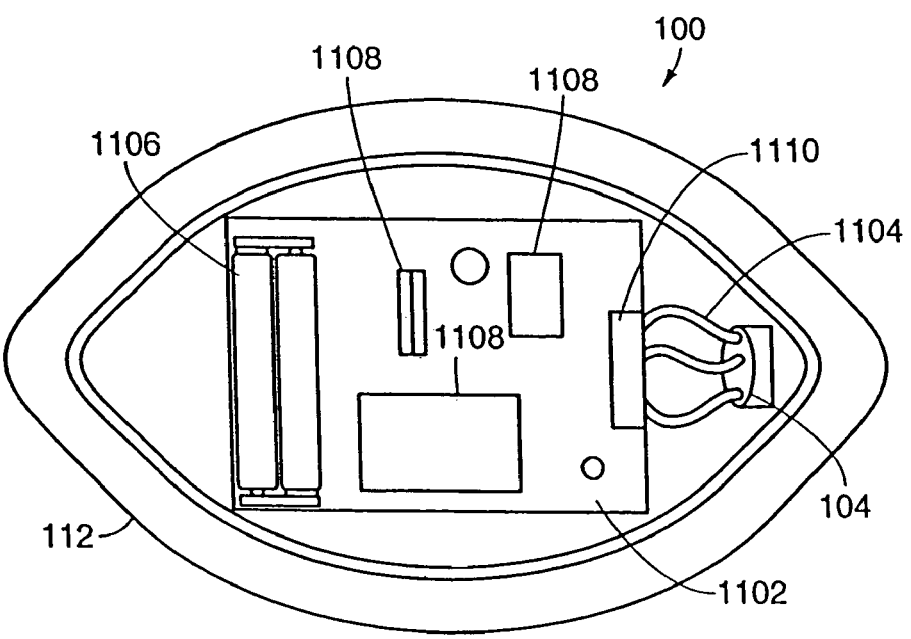
FIG. 11 is an illustrative top view of a percutaneous access device according to another embodiment of the invention.
Figure 12:
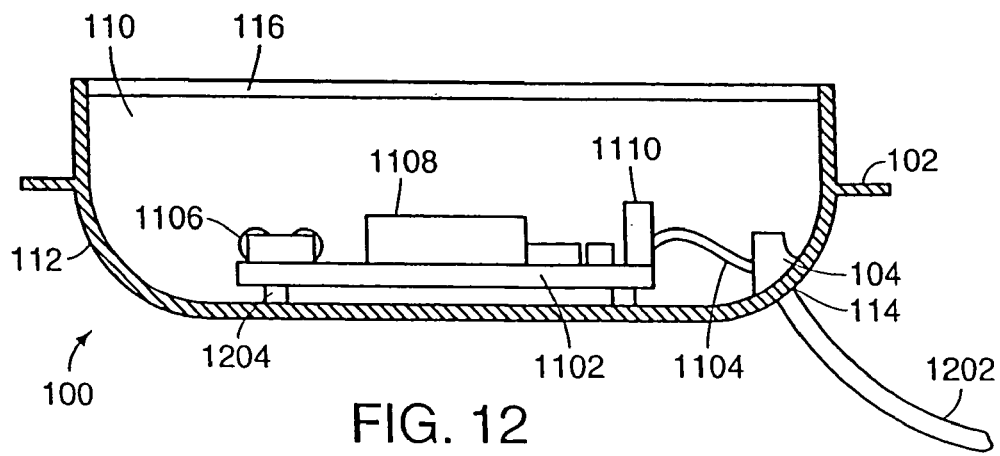
FIG. 12 is an illustrative cross-sectional side view of the percutaneous access device of FIG. 11.
Figure 14:
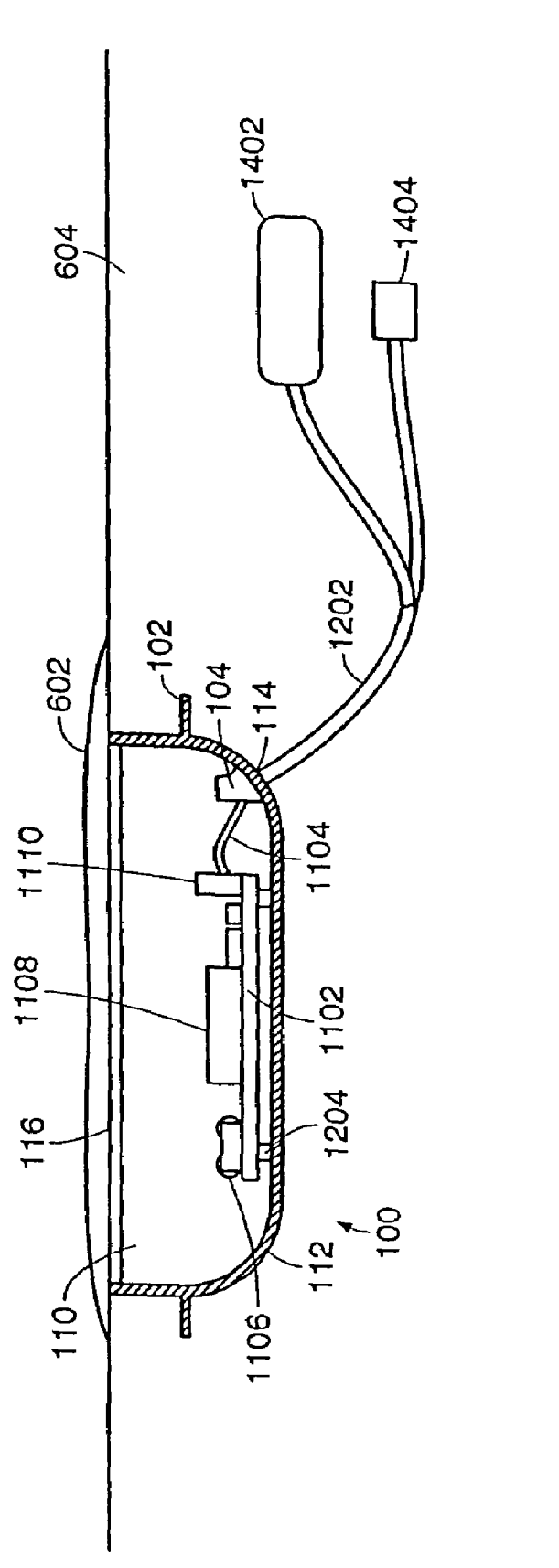
FIG. 14 is an illustrative cross-sectional side view of the percutaneous access device shown in FIG. 11, implanted in a patient and connected to internally-implanted medical devices.

Referring to FIGS. 11, 12, and 14, in another embodiment, the cavity 110 of the access device 100 is used to store a small printed circuit board 1102 including electronics 1108 and/or a battery 1106 used in conjunction with one or more medical devices implanted in a patient, such as a pacemaker 1402 and/or a sensor 1404, for example. In this configuration, the connector 104 is an electrical connector. The connector 104 is positioned such that the connector 104 is disposed substantially within the cavity 110. Specifically, in some embodiments, a small portion of the connector 104 can extend out of the first opening 116. However, in other embodiments, no portion of the connector 104 extends out of the first opening 116 and is disposed entirely within the cavity 110.

Wires (or optical fiber) 1202 from the connector 104 extend subcutaneously from the housing 112 and connect to the pacemaker 1402 and/or sensor 1404. Wires (or optical fiber) 1104 extending from the connector 104 inside the cavity 110 connect to a connector 1110 on the printed circuit board 1102. The printed circuit bard 1102 is coupled to the housing 112 inside the cavity 110 by mounting posts 1204.

Figure 16A:
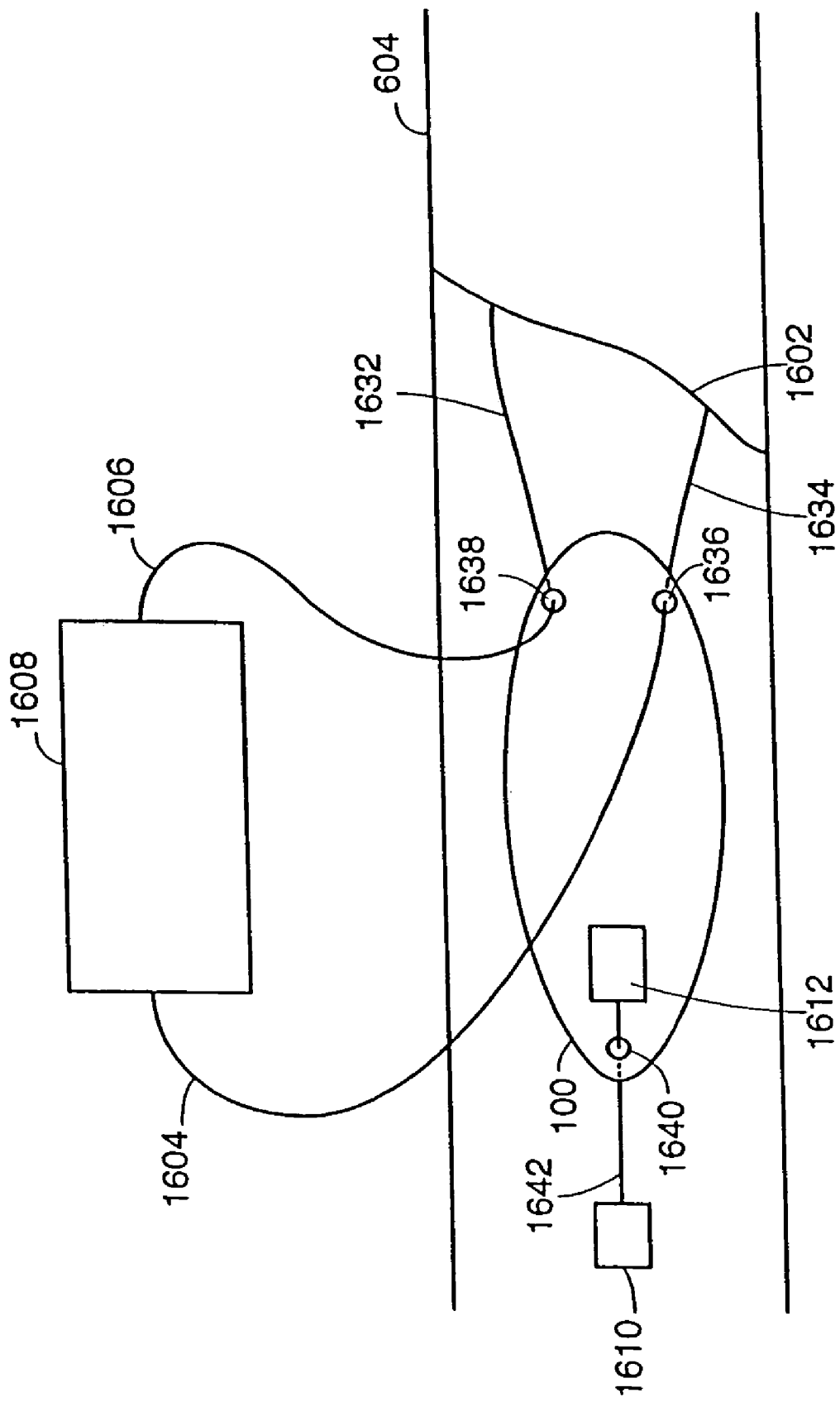
FIG. 16A is an illustrative diagram of a percutaneous access device implanted in a patient and connected to internal and external medical devices, according to one embodiment of the invention.
Figure 16B:
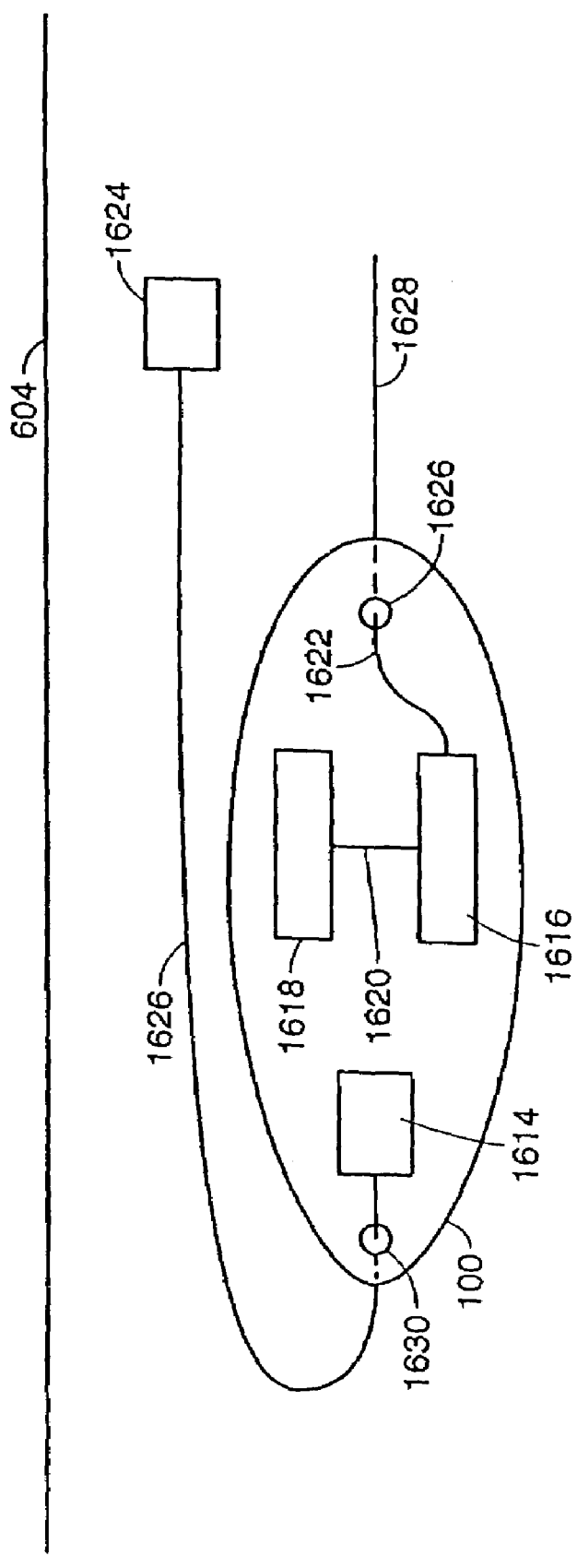
FIG. 16B is an illustrative diagram of the percutaneous access device shown in FIG. 16A, implanted in a patient and connected to internal medical devices.

Referring to FIG. 16B, in one embodiment, an infusion pump 1616 and a medication reservoir 1618 can be housed in the cavity 110 of the access device 100. The medication reservoir 1618 supplies medication to the infusion pump 1616 through tube 1620. The infusion pump 1616 pumps medication though tube 1622, through luer connector 1626, and through catheter 1628 and into the patient's body 604. Electronics 1614 (housed in the cavity 110) can include a battery to power the infusion pump 1616 and control circuitry to control the infusion pump 1616. In addition to the luer connector 1626, the access device 100 can also include one or more electronic connectors, such as electrical connector 1630. Electronic connector 1630 can be used to connect power and control electronics to a sensor 1624, or other device (via wires or optical fiber 1626) implanted in the patient, for example. In another embodiment, the entire cavity 110 can be used as a medication reservoir.

Referring to FIG. 14, in another embodiment, the printed circuit board 1102 (housed in the cavity 110) can include control circuitry 1108 and a battery 110 to control and power a pacemaker 1402 implanted in a patient's body 604. In this configuration, the battery 1110 can be replaced without surgery by simply removing the housing cover 602, replacing the battery 1110, and then replacing the cover 602. Similarly, the electronics 1108 controlling the pacemaker 1402 can also be repaired and/or adjusted with surgery. In other embodiments, the wires 1202 extending into the patent's body 604, can fan out to connect to multiple medical devices such as the pacemaker 1402 and one or more sensors 1404. In still other embodiments, the access device 100 can include multiple electronic connectors 104.

As previously described, the electronics 1108 on the printed circuit board 1102 can include control and memory electronics for various sensors, such as pressure sensors and urine pH sensors for example. In another embodiment, these sensors (along with control circuitry and power) can be housed in the cavity 100, and the fluid to be analyzed (blood or urine, for example) is brought into the cavity 100 via an inlet luer connector and pumped back into the body via an outlet luer connector.

Referring to FIG. 16A, in still another embodiment, the access housing 100 can include any combination of connectors. For example, the access housing 100 can include an inlet luer connector 1638 and an outlet luer connector 1636. The inlet connector 1638 is connected to a catheter 1632 which is also connected to a vein 1602. The outlet connector 1636 is connected to a catheter 1634 which is also connected to the vein 1602. The inlet connector 1638 is also connected to tube 1606 which is connected to a blood purification device 1608 external to the patient 604. The outlet connector 1636 is also connected to a tube 1604 which is also connected to the blood purification device 1608. In operation, the blood purification device 1608 draws blood through the catheter 1632, through the inlet connector 1638, through the tube 1606 and into the blood purification device. After the blood is purified, the blood purification device 1608 pumps the purified blood through tube 1604, through outlet connector 1636, through catheter 1634 and back into the vein 1602. Further, the access device 100 can include an electronic connector 1640 which connects control and power electronics 1612 to a medical device (via wires or optical fiber 1642) such as a blood press sensor 1610 implanted in the patient 604.

In another embodiment, the cavity 110 of the access device 100 can be configured to house various electro-mechanical components of an artificial heart implanted in a patient. In this embodiment, the electro-mechanical parts are accessible (without requiring surgery) by removing the housing cover 602.

In other embodiments, the access device 100 can include electronics capable of wireless communication. In this embodiment, physicians and/or medical personnel can wirelessly communicate with electronics stored in the cavity 110 (without removing the cover 602) to download data from various sensors implanted in a patient, for example. The physician can also download a status of a medication reservoir or a status of battery power. Further, the electronics housed in the cavity used to communicate with and control various implanted medical devices can do so wirelessly. For example, a sensor used for sensing the pressure in a particular artery can transmit sensor data wirelessly to an electronic storage element in the cavity 110, or control circuitry used for controlling a pacemaker can transmit control signals wirelessly to the pacemaker.

In another embodiment, sensor signals can be transmitted through a fluid. For example, a pressure sensor is housed within the cavity 110. The sensor is in physical communication with a proximal portion of an elongated membrane that contains a fluid. The elongated membrane extends outside the cavity 110 into the interior of the patient. A pressure change in the patient causes pressure on a distal portion of the membrane which, in turn, causes the fluid within the membrane to flow back to the proximal portion of the membrane and be detected by the pressure sensor.

Figure 15A:
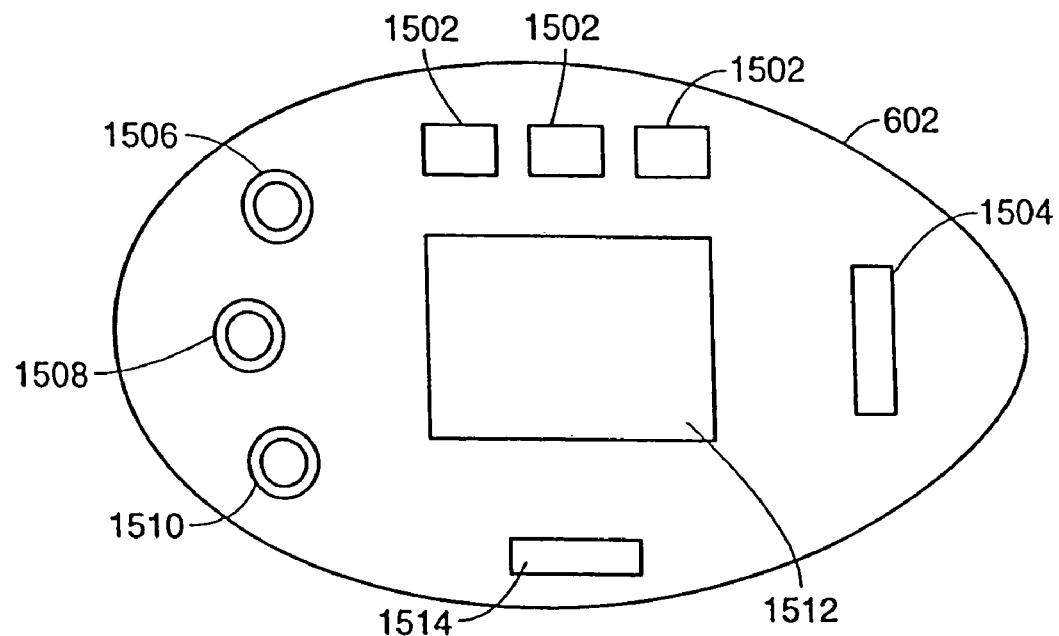
FIG. 15A is an illustrative top view of a housing cover, according to one embodiment of the invention.
Figure 15B:
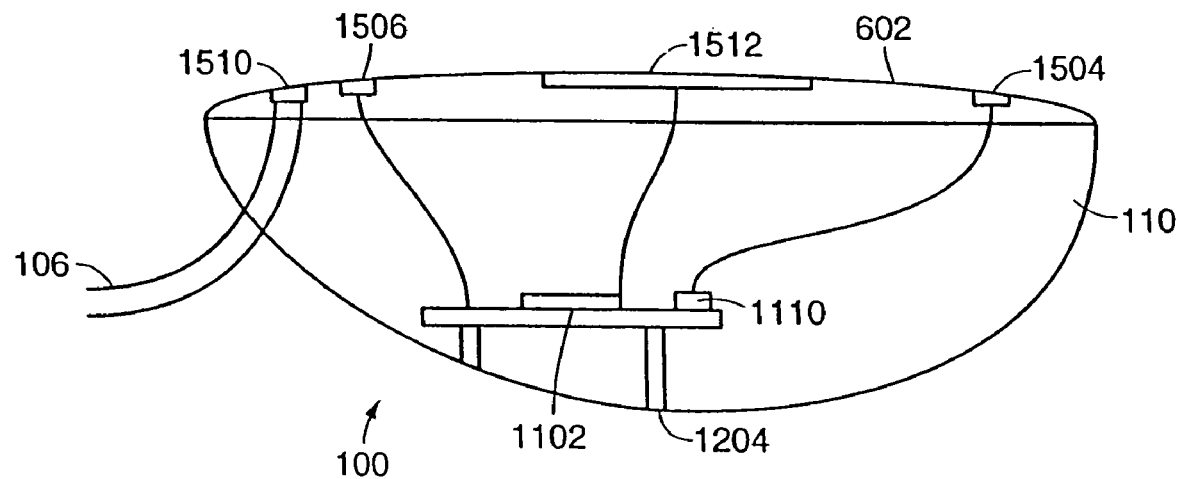
FIG. 15B is an illustrative cross-sectional side view of a housing including the housing cover shown in FIG. 15A.

Referring to FIGS. 15A and 15B, in another embodiment, the housing cover 602 can include low-profile electronic connectors 1506 and/or fiber optics connectors 1508 which can be used to access and read out sensor data stored in a memory chip on the printed circuit board 1102 without having to remove the housing cover 602. The housing cover 602 can also include a low-profile luer connector 1510 which enables a fluid connection to the cavity 110. Such a fluid connection enables a physician and/or medical personnel to access a medical device implanted in the patient (through the cavity 110) or refill a medication reservoir within the cavity 110 without having to remove the housing cover 602. Further, the housing cover 602 can also include indicator LEDs 1502 to indicate low battery power or low medication reservoir levels, for example. The housing cover 602 can also include a battery connector 1502 to enable recharging of a battery 1110 stored in the cavity 110 without having to remove the cover 602. The housing cover 602 can also include a low-profile liquid crystal or LED display for reading sensor data, providing a status of battery power, or providing a status of a medication reservoir stored in the cavity 110, for example. Moreover, the housing cover 602 can include an infrared or wireless communication port 1514 to allow wireless communication with electronics stored within the cavity 110 and/or medical devices implanted in the patient.

Some of the benefits of utilizing the access device 100 to store such electronics and/or batteries include nonsurgical accessibility of the electronics for repair and/or replacement, nonsurgical battery replacement, patient comfort, and reduced chance of infection from electronic components.

Variations, modifications, and other implementations of what is described herein will occur to those of ordinary skill in the art without departing from the spirit and the scope of the invention. Accordingly, the invention is not to be defined solely by the preceding illustrative description.

What is claimed is:

1. An access port for implantation into a patient, comprising:
   a housing defining a cavity therein, the housing including a first opening extending from an exterior of the housing to the cavity and a second opening extending from an exterior of the housing to the cavity wherein, when implanted in the body in an operative position, the first opening faces a skin of the patient and the second opening faces away from the skin toward an interior of the patient;
   a removable connector including a distal end sized to be received within an access device, the removable connector including a locking element which, when the removable connector is received within the second opening, locks the removable connector to the housing.

2. The access port according to claim 1, further comprising a cover sealing the first opening when access to the access device is not desired.

3. The access port according to claim 2, wherein the cover is shaped to substantially conform to a shape of a portion of skin surrounding the first opening.

4. The access port according to claim 2, wherein the cap includes a lock for locking the cap in place on the housing.

5. The access port according to claim 1, wherein the removable connector comprises a connection tube.

6. The access port according to claim 1, wherein the locking element includes at least one projection which mates with a corresponding projection on a surface of the housing adjacent to the second opening.

7. The access port according to claim 1, wherein the removable connector further comprises a cap selectively opening and closing an opening of the removable connector.

8. The access port according to claim 1, wherein the removable connector is telescopic for extension out of the cavity to establish access to the access device.

9. The access port according to claim 1, wherein the housing is substantially elliptical.

10. The access port according to claim 1, wherein the removable connector includes a valve and an extension portion wherein, when the valve is in a first position, a lumen of the valve is aligned with a lumen of the extension portion and, when in a second position, the lumen of the valve is sealed from the lumen of the extension portion.

11. The access port according to claim 10, wherein the valve pivots between the first and second positions.

12. A method of accessing areas within a patient's skin, comprising:
   making an incision through the patient's skin;
   implanting through the incision a port with a cavity formed therein, the port including a first opening extending from an exterior thereof to the cavity and a second opening extending from an exterior thereof to the cavity, the port being implanted so that the first opening faces the skin and the second opening faces away from the skin toward an interior of the patient; and
   inserting into the second opening a connector adapted to couple to an access device.

13. The method according to claim 12, wherein the incision is a substantially straight incision.

14. The method according to claim 12, further comprising the step of locking the connector to the port.

15. The method according to claim 14, wherein the connector is locked to the port by engaging a projection on the connector with a corresponding projection on the port.

* * * * *